(12) United States Patent
Kinsella et al.

(10) Patent No.: US 6,533,779 B2
(45) Date of Patent: Mar. 18, 2003

(54) PMR CATHETER AND ASSOCIATED METHODS

(75) Inventors: Bryan Kinsella, Seattle, WA (US); Lauri DeVore, Seattle, WA (US); Lucas Gordon, Redmond, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/760,876

(22) Filed: Jan. 16, 2001

(65) Prior Publication Data

US 2002/0095148 A1 Jul. 18, 2002

(51) Int. Cl.⁷ .............................................. A61B 18/14
(52) U.S. Cl. ........................... 606/41; 606/45; 606/49; 607/105; 607/113; 607/122
(58) Field of Search ........................... 606/41, 45, 49; 607/122, 105, 113

(56) References Cited

U.S. PATENT DOCUMENTS

| | | | |
|---|---|---|---|
| 4,682,596 A * | 7/1987 | Bales et al. ..................... 606/45 |
| 5,451,224 A | 9/1995 | Goble et al. .................... 606/48 |
| 5,593,406 A | 1/1997 | Eggers et al. ................... 606/46 |
| 5,697,882 A | 12/1997 | Eggers et al. .................. 604/114 |
| 5,766,164 A | 6/1998 | Mueller et al. ................. 606/15 |
| 5,769,843 A | 6/1998 | Abela et al. .................... 606/10 |
| 5,782,760 A * | 7/1998 | Schaer .......................... 606/41 |
| 5,782,823 A | 7/1998 | Mueller ......................... 606/7 |
| 5,785,702 A | 7/1998 | Murphy-Chutorian et al. . 606/7 |
| 5,800,450 A | 9/1998 | Lary et al. .................... 606/180 |
| 5,807,384 A | 9/1998 | Mueller .......................... 606/7 |
| 5,807,388 A | 9/1998 | Jeevanandam et al. ........ 606/15 |
| 5,810,836 A | 9/1998 | Hussein et al. .............. 606/108 |
| 5,827,203 A | 10/1998 | Nita .............................. 601/2 |
| 5,832,929 A | 11/1998 | Rudko et al. ................ 128/898 |
| 5,840,059 A | 11/1998 | March et al. .................. 604/53 |
| 5,840,075 A | 11/1998 | Mueller et al. ................. 606/7 |
| 5,855,577 A | 1/1999 | Murphy-Chutorian et al. . 606/7 |
| 5,860,951 A | 1/1999 | Eggers et al. .................. 604/49 |
| 5,871,469 A | 2/1999 | Eggers et al. ................. 604/114 |
| 5,871,495 A | 2/1999 | Mueller ....................... 606/185 |
| 5,873,366 A | 2/1999 | Chim et al. .................. 128/898 |
| 5,873,855 A | 2/1999 | Eggers et al. ................. 604/114 |
| 5,878,751 A | 3/1999 | Hussein et al. ............. 128/898 |
| 5,885,272 A | 3/1999 | Aita et al. ....................... 606/7 |
| 5,885,276 A | 3/1999 | Ammar et al. ................ 606/21 |
| 5,891,133 A | 4/1999 | Murphy-Chutorian ......... 606/7 |
| 5,893,848 A | 4/1999 | Negus et al. .................. 606/41 |
| 5,906,615 A | 5/1999 | Thompson .................... 606/45 |
| 6,056,743 A * | 5/2000 | Ellis et al. .................... 606/15 |
| 6,066,134 A | 5/2000 | Eggers et al. ................. 606/32 |
| 6,093,185 A | 7/2000 | Ellis et al. .................... 606/28 |
| 6,120,476 A | 9/2000 | Fung et al. .................... 604/95 |
| 6,162,214 A | 12/2000 | Mueller et al. ................ 606/15 |
| 6,168,624 B1 | 1/2001 | Sudai ........................ 623/3.21 |
| 6,198,974 B1 | 3/2001 | Webster, Jr. ................ 607/122 |
| 6,217,575 B1 | 4/2001 | DeVore et al. ................ 606/41 |
| 6,224,592 B1 | 5/2001 | Eggers et al. ................. 606/32 |

FOREIGN PATENT DOCUMENTS

| | | |
|---|---|---|
| EP | 0 868 923 A2 | 10/1998 |
| WO | WO 98/19614 | 5/1998 |
| WO | WO 98/25533 | 6/1998 |
| WO | WO 98/27877 | 7/1998 |
| WO | WO 98/30144 | 7/1998 |

(List continued on next page.)

Primary Examiner—Lee Cohen
(74) Attorney, Agent, or Firm—Christensen O'Connor Johnson Kindness PLLC

(57) ABSTRACT

A PMR catheter and associated methods are disclosed. A catheter in accordance with the present invention comprised, an elongate shaft having a proximal portion, a distal portion, and a lumen extending through at least the distal portion thereof, an electrode disposed proximate the distal portion of the elongate shaft, and an electrode lumen defined by the electrode and being in fluid communication with the lumen of the elongate shaft.

18 Claims, 13 Drawing Sheets

FOREIGN PATENT DOCUMENTS

| | | |
|---|---|---|
| WO | WO 98/31281 | 7/1998 |
| WO | WO 98/33557 | 8/1998 |
| WO | WO 98/38916 | 9/1998 |
| WO | WO 98/38925 | 9/1998 |
| WO | WO 98/39038 | 9/1998 |
| WO | WO 98/49963 | 11/1998 |
| WO | WO 98/49964 | 11/1998 |
| WO | WO 99/04708 | 2/1999 |
| WO | WO 99/04709 | 2/1999 |
| WO | WO 99/07296 | 2/1999 |
| WO | WO 99/08612 | 2/1999 |

* cited by examiner

PMR CATHETER AND ASSOCIATED METHODS

FIELD OF THE INVENTION

The present invention relates generally to devices and methods for promoting blood circulation to the heart muscle. More particularly, the present invention relates to devices and methods for forming holes or channels in the walls of a heart chamber such as those created during a percutaneous myocardial revascularization (PMR) procedure.

BACKGROUND OF THE INVENTION

Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical.

When techniques which treat individual lesion are not practical a technique know as percutaneous myocardial revascularization (PMR) may be used to improve the oxygenation of the myocardial tissue. A PMR procedure generally involves the creation of holes, craters or channels directly into the myocardium of the heart. PMR was inspired in part by observations that reptilian heart muscles are supplied with oxygen primarily by blood perfusing directly from within heart chambers to the heart muscle. This contrasts with the human heart, which is supplied by coronary vessels receiving blood from the aorta. Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenisis. In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

SUMMARY OF THE INVENTION

The present invention relates generally to devices and methods for promoting blood circulation to the heart muscle. More particularly, the present invention relates to devices and methods for forming holes or channels in the walls of a heart chamber such as those created during a percutaneous myocardial revascularization (PMR) procedure. One embodiment of a catheter in accordance with the present invention includes an elongate shaft comprising a sheath disposed about an elongate shaft. The elongate shaft includes a distal end and a proximate end. The catheter also includes a distal port defined by an electrode disposed proximate the distal end of the elongate shaft.

A hub is disposed about the elongate shaft and the sheath proximate the proximal end of the catheter. The hub includes a proximal port, a connector, and a strain relief. The proximal port may be utilized to couple the catheter to a fluid source. In a presently preferred embodiment, the elongate shaft defines a lumen which is in fluid communication with the proximal port and the distal port of the catheter. A connector may be utilized to couple the catheter to an energy source. In a presently preferred embodiment the connector includes a connector pin which is electrically coupled to electrode.

A PMR system in accordance with the present invention may include a tube fitting adapted to couple with the proximal port of the catheter. The proximal port may be utilized to couple the catheter to a fluid source. The lumen of the elongate shaft is sealed proximate the proximal end of the elongate shaft. Fluid from a fluid source may enter the lumen of the elongate shaft via an aperture and exit via the distal port of the catheter.

In a presently preferred embodiment, the hub defines a connector lumen and the elongate shaft extends into the connector lumen forming a connector pin. In a presently preferred embodiment, connector pin is electrically coupled to the electrode of the catheter via the elongate shaft. A PMR system in accordance with the present invention may include a mating connector which is adapted to couple with the connector of the catheter. When a connector and mating connector are mated, an electrically connection may be formed between a lead wire and the connector pin.

The electrode may comprise a tip member which is fixed to the distal end of the elongate shaft. In a presently preferred embodiment, the tip member defines a tip lumen which is in fluid communication with the lumen of the elongate shaft. A coil comprising a plurality of turns is disposed about a portion of the elongate shaft. The coil is fixed to the tip member proximate a distal end thereof. The sheath may be disposed about the coil and elongate shaft.

An additional embodiment of a catheter in accordance with the present invention may include an elongate shaft comprising a sheath disposed about a coil comprising a plurality of turns, a lumen, and a wire disposed in the lumen. A hub assembly may be disposed about the elongate shaft assembly proximate the proximal end thereof. In a presently preferred embodiment, the hub assembly includes a strain relief and a positioning mechanism. The positioning mechanism includes a slider which is disposed in sliding engagement with a guiding surface defined by a hub of the hub assembly. The slider is coupled to the wire proximate a proximal end thereof. The slider may be moved from a first position to a second position. The slider may also be positioned at points between the first position and the second position.

In a presently preferred embodiment, the wire is held in tension when the slider is disposed in the first position. Also in a presently preferred embodiment, the wire includes a curved portion (not shown) proximate the distal end thereof. In this presently preferred embodiment, the curved portion of the wire is biased to assume a generally curved shape. The wire may be held in tension by the positioning mechanism. When the wire is held in tension adjacent turns of the coil may be urged into close proximity with each other, and the wire may be pulled straight (more or less). When the slider is in placed in the second position B the curved portion of wire is free to return to its unbiased, substantially curved shape.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
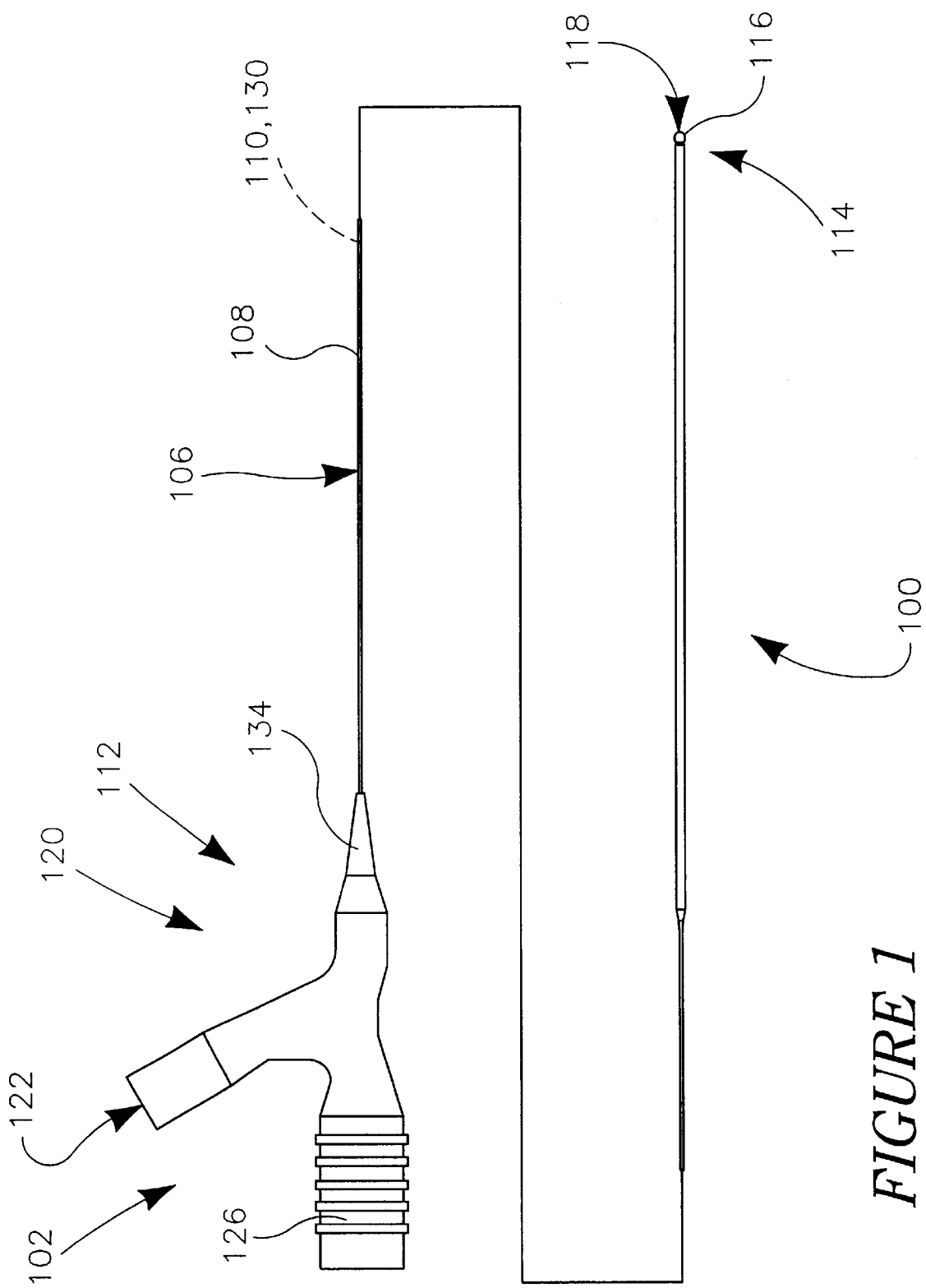
FIG. 1 is a plan view of a catheter in accordance with an exemplary embodiment of the present invention.

FIG. 1 is a plan view of a catheter 100 in accordance with an exemplary embodiment of the present invention. Catheter 100 includes an elongate shaft assembly 106 comprising a sheath 108 disposed about an elongate shaft 110. Elongate shaft 110 includes a distal end 114 and a proximal end 112. Catheter 100 also includes an electrode 116 disposed proximate distal end 114 of elongate shaft 110. Electrode 116 includes a distal port 118.

A hub 120 is disposed about elongate shaft 110 and sheath 108 proximate a proximal end 102 of catheter 100. Hub 120 includes a proximal port 122, a connector 126, and a strain relief 134. Proximal port 122 may be utilized to couple catheter 100 to a fluid source. In the embodiment of FIG. 1, elongate shaft 110 defines a lumen 130 which is in fluid communication with proximal port 122 and distal port 118 of catheter 100. Connector 126 may be utilized to couple catheter 100 to an energy source. In the embodiment of FIG. 1, connector 126 includes a connector pin (not shown in FIG. 1) which is electrically coupled to electrode 116.

Figure 2:
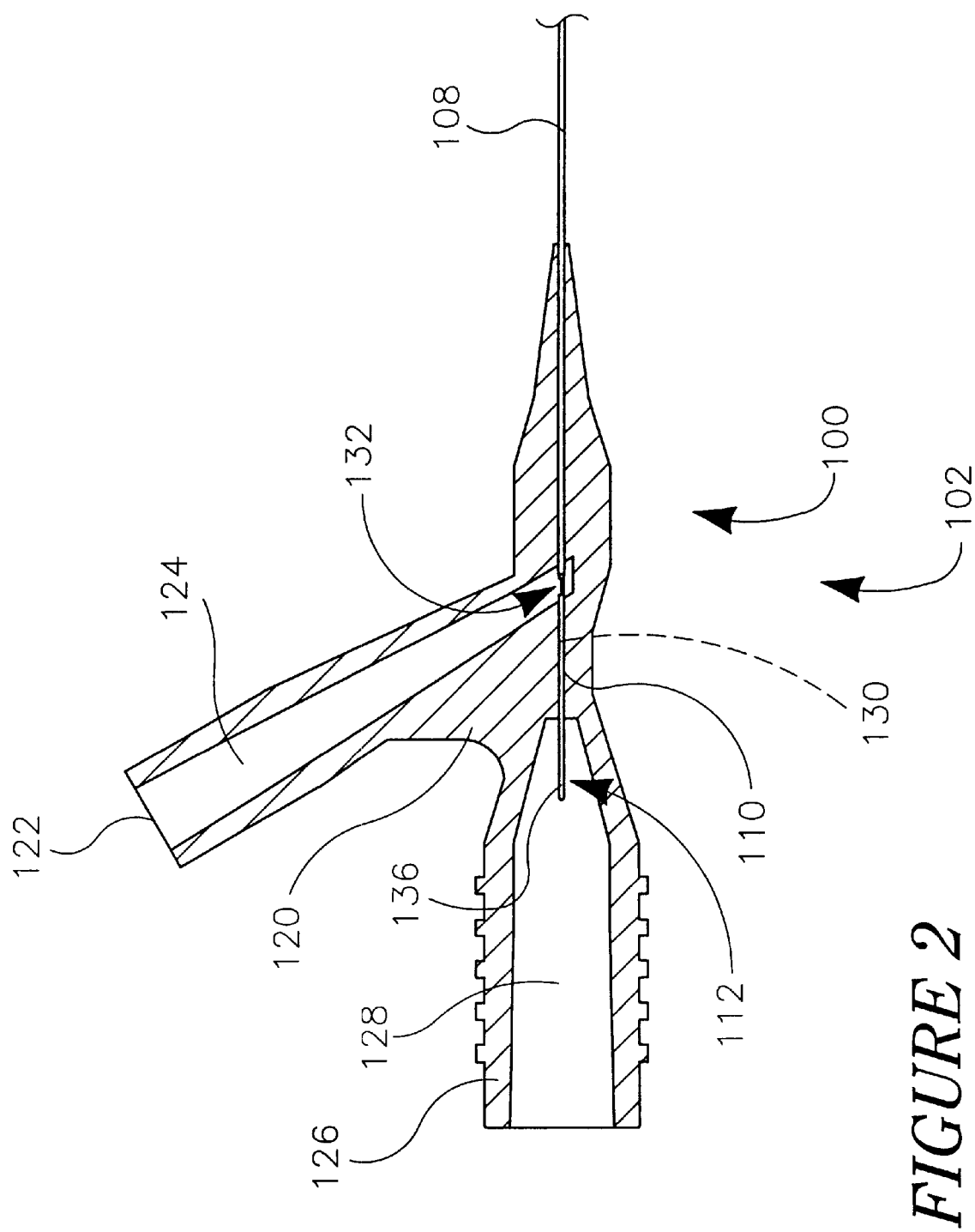
FIG. 2 is a cross sectional view of a portion of a catheter in accordance with an exemplary embodiment of the present invention.

FIG. 2 is a cross sectional view of a portion of catheter 100 proximate proximal end 102 thereof. As described previously, hub 120 is disposed about elongate shaft 110 and sheath 108 proximate proximal end 102 of catheter 100. In FIG. 2 it may be appreciated that proximal port 122 is in fluid communication with a hub lumen 124 defined by hub 120. Hub lumen 124 is in fluid communication with an aperture 132 defined by elongate shaft 110. Aperture 132 is also in fluid communication with lumen 130 of elongate shaft 110.

A PMR system in accordance with the present invention may include a tube fitting adapted to couple with proximal port 122 of hub 120. Proximal port 122 of hub 120 may be utilized to couple catheter 100 to a fluid source. Lumen 130 of elongate shaft 110 is sealed proximate proximal end 112 of elongate shaft 110. Fluid from a fluid source may enter lumen 130 via aperture 132 and exit via distal port 118 of catheter 100.

In FIG. 2, it may also be appreciated that connector 126 of hub 120 defines a connector lumen 128. Elongate shaft 110 extends into connector lumen 128 forming a connector pin 136. In a presently preferred embodiment, connector pin 136 is electrically coupled to electrode 116 of catheter 100 via elongate shaft 110. A PMR system in accordance with the present invention may include a mating connector which is adapted to couple with connector 126 of catheter 100. An electrical connection may be formed between a lead wire and connector pin 136 by coupling connector 126 with a mating connector.

Figure 3:
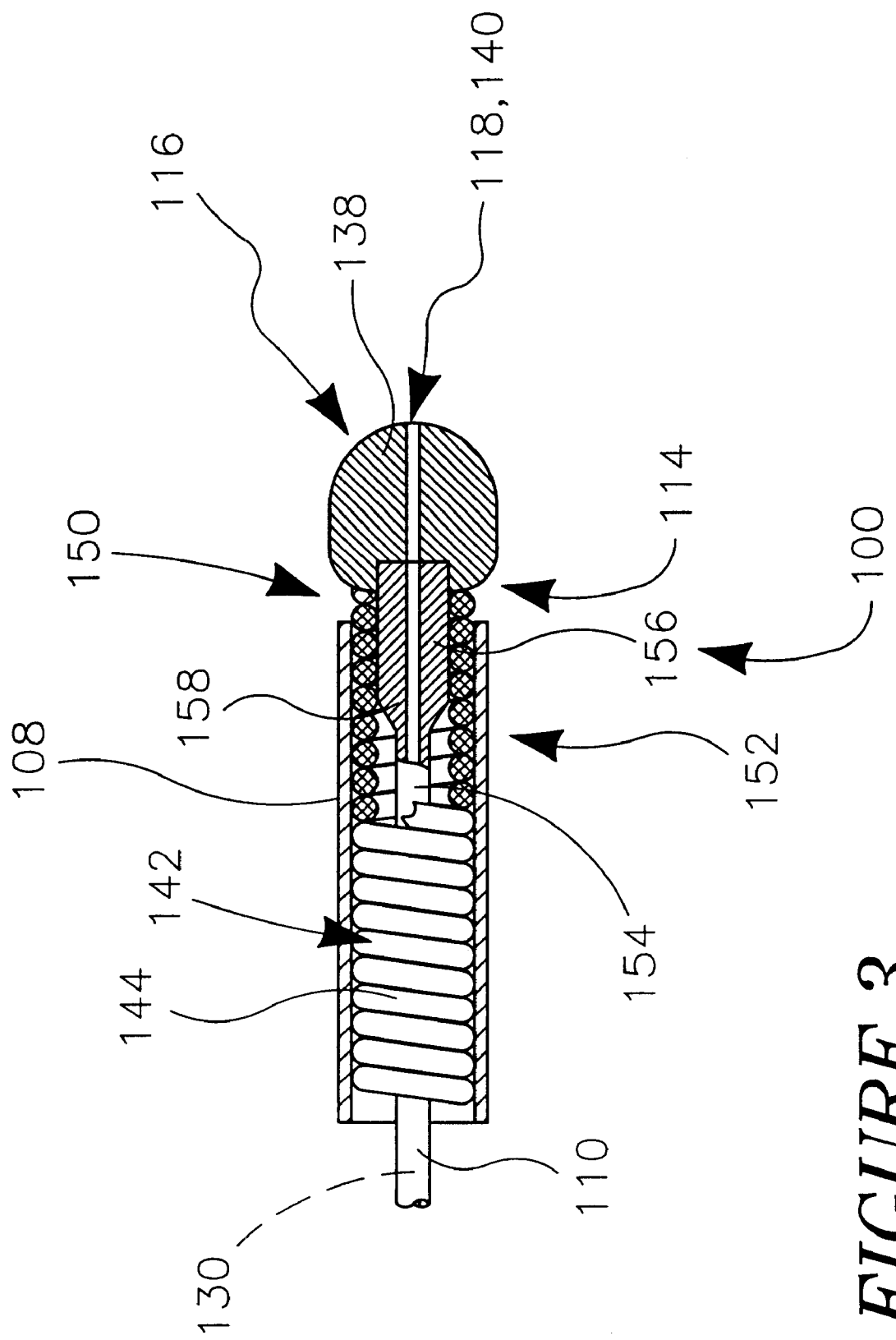
FIG. 3 is a cross-sectional view of a distal portion of a catheter in accordance with an exemplary embodiment of the present invention.

FIG. 3 is a cross-sectional view of a distal portion of catheter 100. In FIG. 3 it may be appreciated that electrode 116 comprises a tip member 138 which is fixed to distal end 114 of elongate shaft 110. Tip member 138 defines a tip lumen 140 which is in fluid communication with lumen 130 of elongate shaft 110 and distal port 118 of catheter 100. In a presently preferred embodiment, tip lumen 140 is disposed proximate the geometric center of electrode 116. During a PMR procedure fluid may be urged out of distal port 118 proximate a wound formed by electrode 116.

A coil 142 comprising a plurality of turns 144 is disposed about a portion of elongate shaft 110. Coil 142 is fixed to tip member 138 proximate a distal end 150 thereof. As shown in FIG. 3, sheath 108 is disposed about coil 142 and elongate shaft 110. Embodiments of the present invention have also been envisioned in which sheath 108 is disposed within a lumen defined by coil 142.

In FIG. 3, it may be appreciated that elongate shaft 110 includes a profiled portion 152. In the embodiment of FIG. 3, profiled portion 152 includes a first diameter 154, a second diameter 156, and a taper 158. Those of skill in the art will appreciate that elongate shaft 110 may include a plurality of diameters and a plurality of tapers without deviating from the spirit and scope of the present invention.

Figure 4:
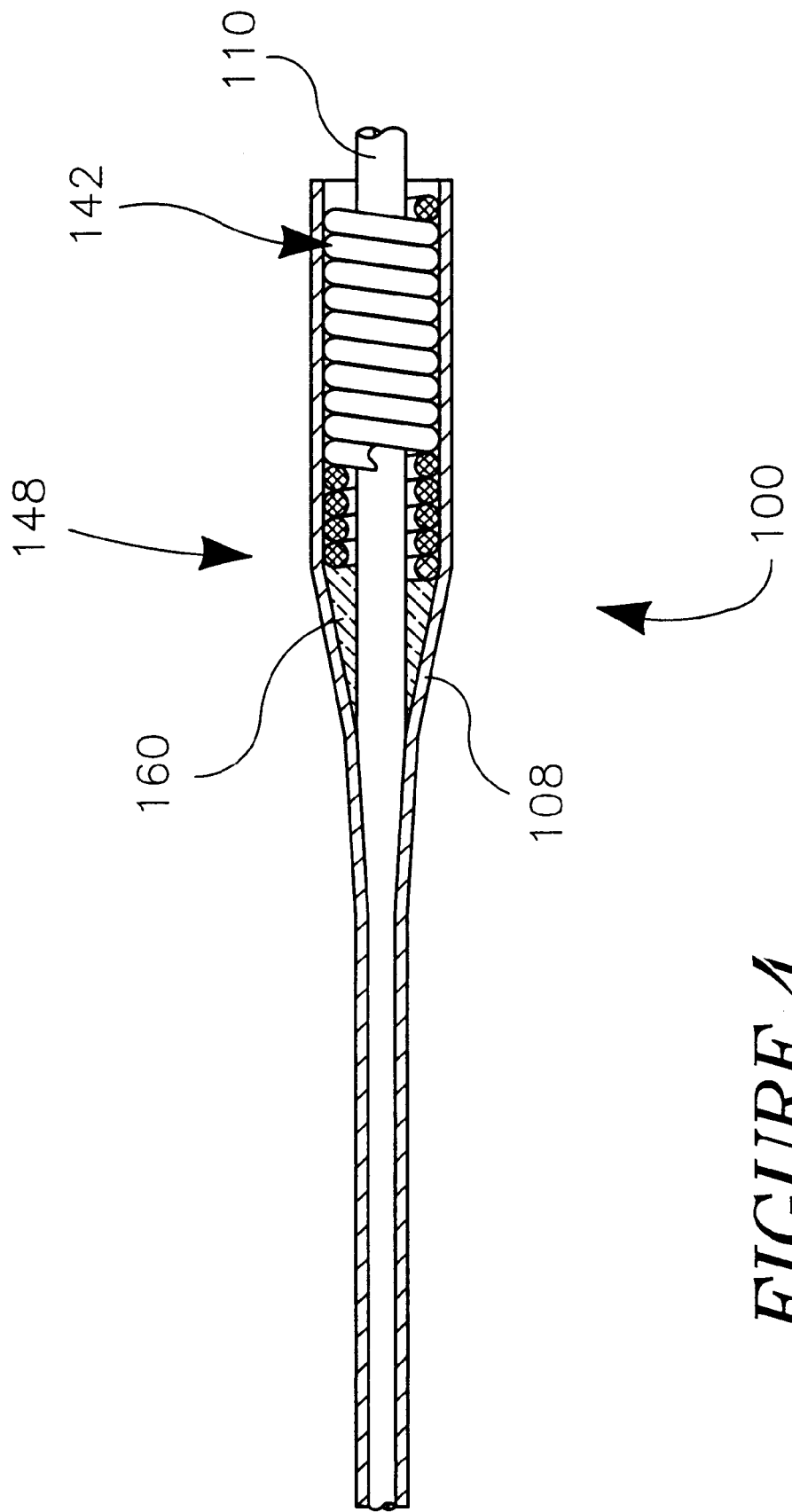
FIG. 4 is a cross sectional view of a portion of a catheter in accordance with an exemplary embodiment of the present invention.

FIG. 4 is a partial cross sectional view of a portion of catheter 100. In FIG. 4 it may be appreciated that a proximal end 148 of coil 142 is fixed to elongate shaft 110 at a joint 160. In a presently preferred embodiment, joint 160 is comprised of solder. Those of skill in the art will appreciate that joint 160 may be comprised of other materials without deviating from the spirit and scope of the present invention. It should also be appreciated that a variety of joining methods are may be utilized without deviating from the spirit and scope of the present invention. Examples of joining methods which may be suitable in some applications include soldering, brazing, welding, and adhesive bonding. Examples of welding processes which may be suitable in some applications include LASER welding, TIG welding, resistance welding, and plasma welding. In a presently preferred embodiment, joint 160 provides a substantially smooth transition between the outer diameter of coil 142 and the outer diameter of elongate shaft 110. Embodiments of the present invention have also been envisioned in which sheath 108 is disposed with a lumen defined by coil 142.

In FIG. 4, sheath 108 is shown overlaying joint 160, elongate shaft 110, and coil 142. In a presently preferred embodiment, sheath 108 is comprised of polytetrafluoroethylene (PTFE) heat shrink tubing. Suitable PTFE heat shrink tubing is commercially available from Zeus Industries of Orangeburg, S.C. and Raychem Corporation of Menlo Park, Calif. Those of skill in the art will appreciate that sheath 108 may be comprised other materials without deviating from the spirit and scope of the present invention. Examples of materials which may be suitable in some applications include: polyethylene (PE), polypropylene (PP), polyvinylchloride (PVC), polyurethane, and polyether block amide (PEBA).

In a presently preferred embodiment, elongate shaft 110 comprises Nitinol. In a presently more preferred embodiment, elongate shaft comprises Nitinol hypodermic tubing. Nitinol is a type of nickel-titanium alloy. Nitinol is commercially available from Memry Technologies (Brookfield, Conn.), TiNi Alloy Company (San Leandro, Calif.), and Shape Memory Applications (Sunnyvale, Calif.). Those of skill in the art will appreciate that elongate shaft 110 may comprise many metallic and non-metallic materials without deviating from the spirit and scope of the present invention. Examples of metallic materials which may be suitable in some applications include stainless steel, tantalum, and titanium.

Figure 5:
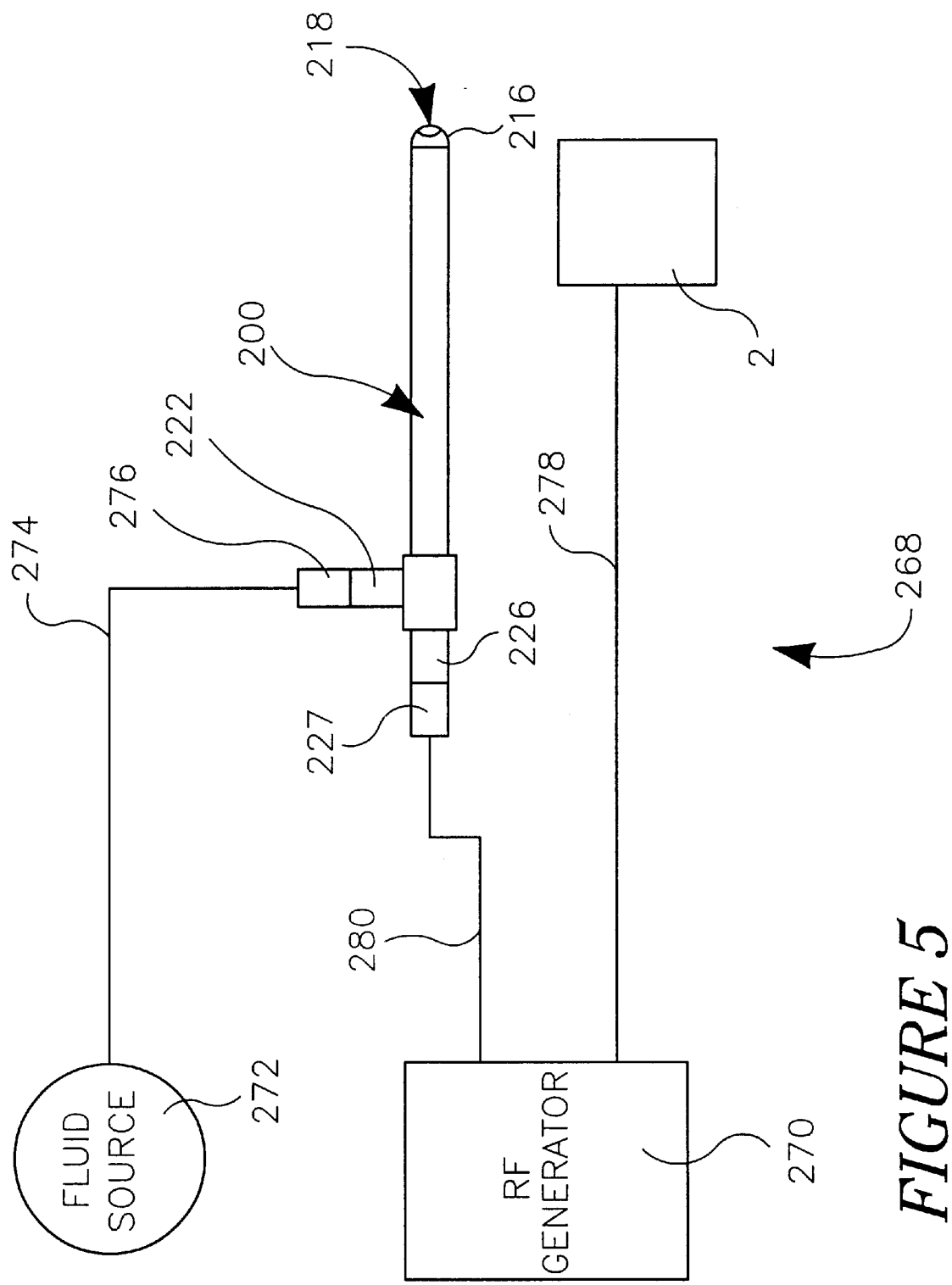
FIG. 5 is a schematic representation of a PMR system in accordance with an exemplary embodiment of the present invention.

FIG. 5 is a schematic representation of a PMR system 268 including a catheter 200 in accordance with the present invention. Catheter 200 includes a proximal port 222 in fluid communication with a distal port 218, and a connector 226 coupled to an electrode 216. An RF generator 270 is coupled to connector 226 of catheter 200 by a mating connector 226 and a lead wire 280. A fluid source 272 is coupled to proximal port 222 of catheter 200 via a conduit 274 and a conduit fitting 276.

PMR system 268 also includes a return electrode coupled to RF generator 270 by a lead wire 278. Return electrode 2 is adapted for connection to the body of a patient. Return electrode 216 in the embodiment of FIG. 5 is pictured as a flat pad. A return electrode of this type typically includes a flexible conductive pad which conforms to the contours of a patient's body. Materials suitable for this conductive pad include metal foil and conductive ink disposed on a polymer substrate. Return electrodes of this type typically are adhered to the outside of a patient's body with an interface material which is both conductive and sticky, such as a hyrodgel adhesive. This configuration of an active electrode disposed on a catheter, and passive electrode pad is sometimes referred to as monopolar. Bipolar embodiments of the present invention have also been envisioned. In a bi-polar configuration, a return, or neutral electrode is disposed in close proximity to the active electrode. For example, a return electrode could be disposed on an outer surface of catheter 200 proximate electrode 216.

Figure 6:
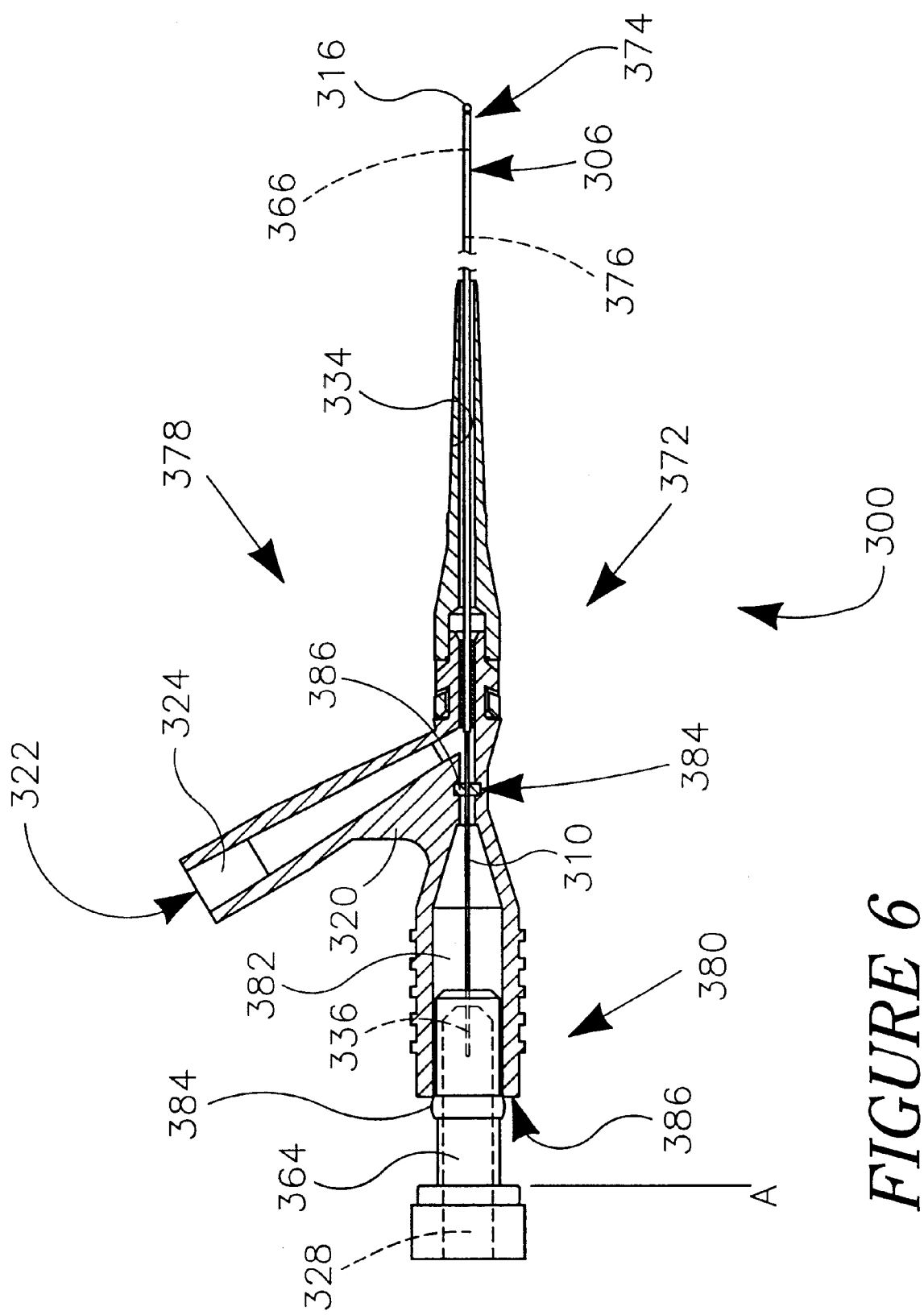
FIG. 6 is a plan view of a catheter in accordance with an exemplary embodiment of the present invention.

FIG. 6 is a plan view of an additional embodiment of a catheter 300 in accordance with the present invention. Catheter 300 includes an elongate shaft assembly 306 having a distal end 374 and a proximate end 372. The construction of shaft assembly 306 is best shown in FIG. 7.

Figure 7:
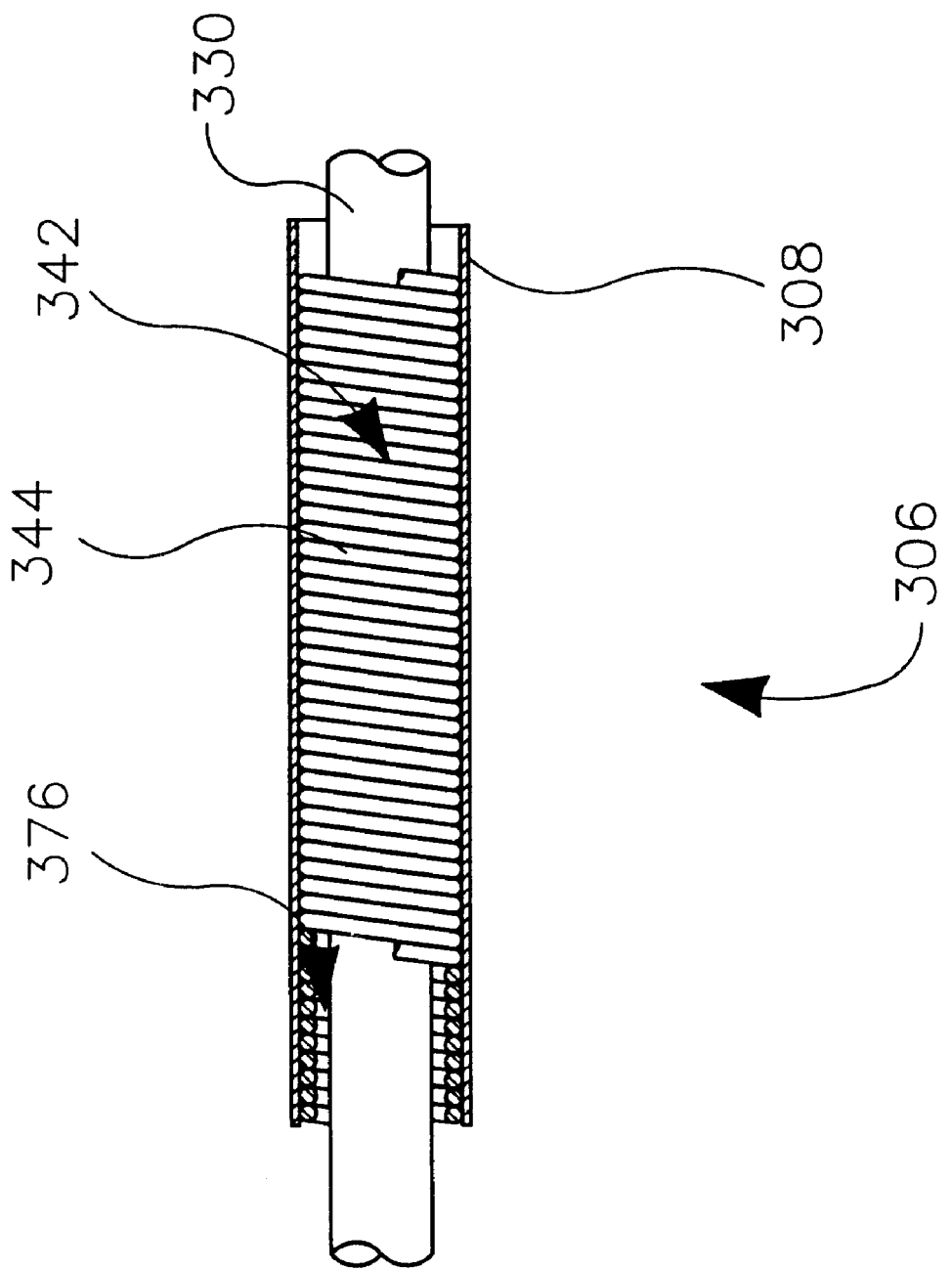
FIG. 7 is a cross sectional view of a portion of a catheter in accordance with an exemplary embodiment of the present invention.

FIG. 7 is a partial cross sectional view of a portion of shaft assembly 306. As shown in FIG. 7, shaft assembly 306 includes a sheath 308 disposed about a coil 342 comprising a plurality of turns 344. Shaft assembly 306 also includes a lumen 376. A wire 310 is disposed in lumen 376 of shaft assembly 306.

Referring again to FIG. 6, a hub assembly 378 is disposed about elongate shaft assembly 306 proximate proximal end 372 thereof. Hub assembly 378 includes a strain relief 334 and a positioning mechanism 380. Positioning mechanism 380 includes a slider 364 which is disposed in sliding engagement with a guiding surface 382 defined by a hub 320 of hub assembly 378. Slider 364 is coupled to wire 310 proximate a proximal end thereof. The position of slider 364 in FIG. 6, is designated with the letter A. With slider 364 disposed in position A, a stop 384 of slider 364 is disposed proximate a proximal surface 386 of hub 320. In the embodiment of FIG. 6, stop 384 comprises an area of generally increased radial dimension.

In a presently preferred embodiment, wire 310 is held in tension when slider 364 is disposed in position A. Also in a presently preferred embodiment, wire 310 includes a curved portion 366 (not shown) proximate the distal end thereof. In this presently preferred embodiment, curved portion 366 of wire 310 is biased to assume a generally curved shape. In the embodiment of FIG. 6, wire 310 is held in tension by positioning mechanism 380. When wire 310 is held in tension adjacent turns 344 of coil 342 are urged into close proximity with each other, and wire 310 is pulled straight (more or less).

Catheter 300 also includes an electrode 316 disposed proximate distal end 374 of elongate shaft assembly 306. Slider 364 defines a connector lumen 328. Wire 310 extends into connector lumen 328 forming a connector pin 336. In a presently preferred embodiment, connector pin 336 is electrically coupled to electrode 316 via wire 310.

Hub 320 also defines a seal groove 384 and a hub lumen 324 which is in fluid communication with lumen 376 of shaft assembly 306. A seal 386 is disposed within seal groove 384 of hub 320. Wire 310 is slidingly disposed within seal 386 and seal 386 forms a seal between wire 310 and hub 320.

Figure 8:
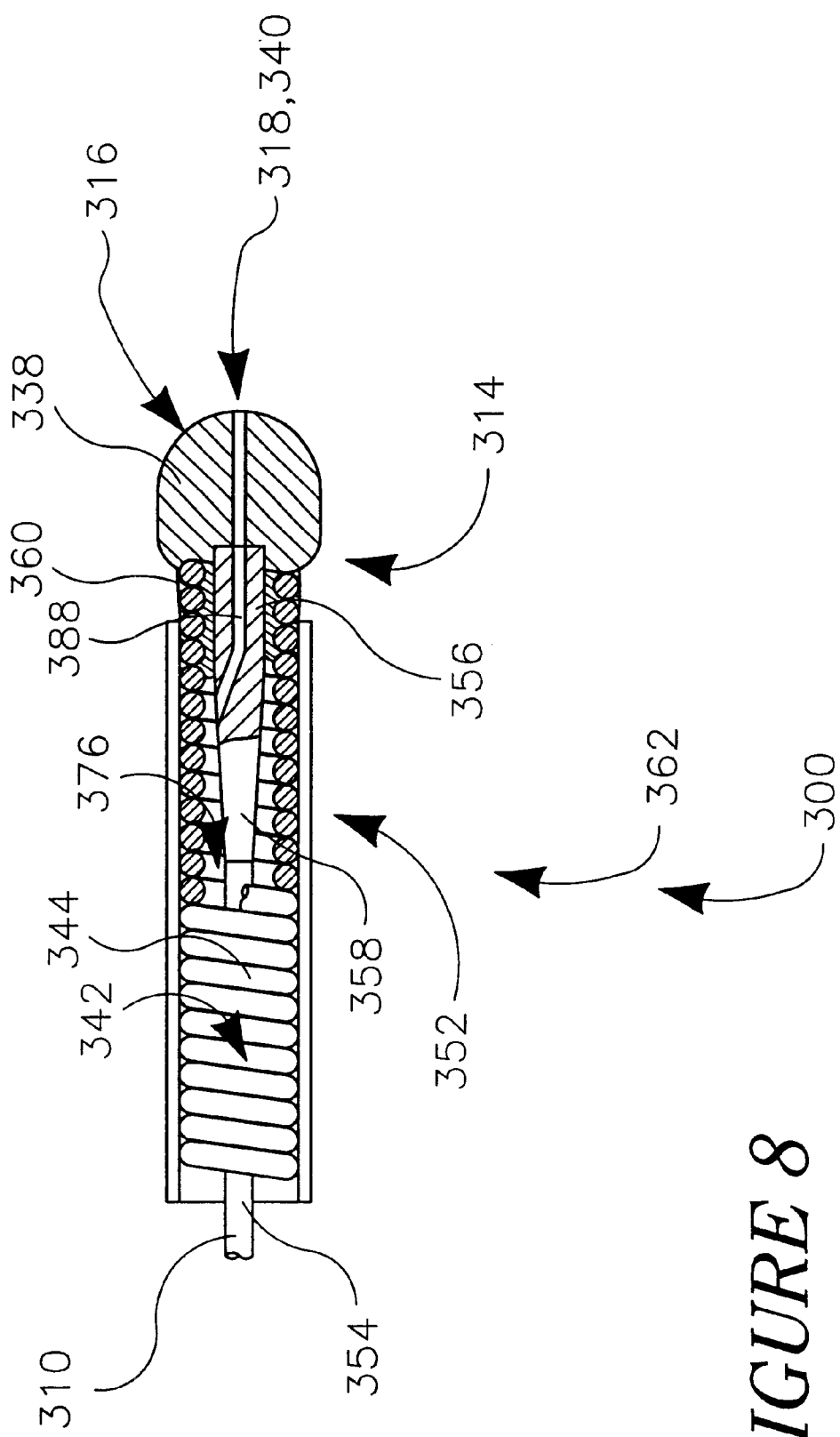
FIG. 8 is a cross sectional view of a portion of a catheter in accordance with an exemplary embodiment of the present invention.

FIG. 8 is a cross-sectional view of a distal portion 362 of catheter 300. In the embodiment of FIG. 8, electrode 316 comprises a tip member 338 which is fixed to distal end 314 of wire 310 and distal end 350 of coil 342. Tip member 338 defines a tip lumen 340 in fluid communication with a distal port 318. Wire 310 defines a wire channel 388 which is in fluid communication with tip lumen 340 and lumen 376 of shaft assembly 306. In a presently preferred embodiment, distal port 318 is disposed proximate the geometric center of electrode 316. During a PMR procedure fluid may be urged out of distal port 318 proximate a wound formed by electrode 316.

In FIG. 8, it may be appreciated that wire 310 includes a profiled portion 352. In the embodiment of FIG. 8, profiled portion 352 includes a first diameter 354, a second diameter 356, and a taper 358. It is to be appreciated that wire 310 may include a plurality of diameters and a plurality of tapers without deviating from the spirit and scope of the present invention. Embodiments of catheter 300 which include a plurality of tip lumens 340 and/or a plurality of wire channels 388 are also possible.

The term "wire", as used in describing wire 310 should not be mistaken as limiting wire 310 to elements having a circular cross section. The cross section of wire 310 may be any number of shapes. For example, the cross section of wire 310 could be rectangular, elliptical, etc. Likewise, the term "wire", as used in describing wire 310 should not be mistaken as being limited to metallic materials. In fact, wire 310 may be comprised of many metallic and non-metallic materials. Examples of metallic materials which may be suitable in some applications include stainless steel, tantalum, and titanium. Wire 310 may also include a nickel-titanium alloy known in the art as Nitinol. Nitinol is commercially available from Memry Technologies (Brookfield, Conn.), TiNi Alloy Company (San Leandro, Calif.), and Shape Memory Applications (Sunnyvale, Calif.). Examples of non-metallic materials which may be suitable in some applications may be found in the list immediately below which is not exhaustive: polycarbonate, poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

Coil 342 is fixed to wire 310 at a joint 360. In the embodiment of FIG. 8, joint 360 connects a distal portion 362 of wire 310 to a distal portion of coil 342 over a plurality of turns 344. In a presently preferred embodiment, joint 360 is comprised of solder. Those of skill in the art will appreciate that other joining methods are possible without deviating from the spirit and scope of the present invention. Examples of methods which may be suitable in some applications include welding and adhesive bonding.

Figure 9:
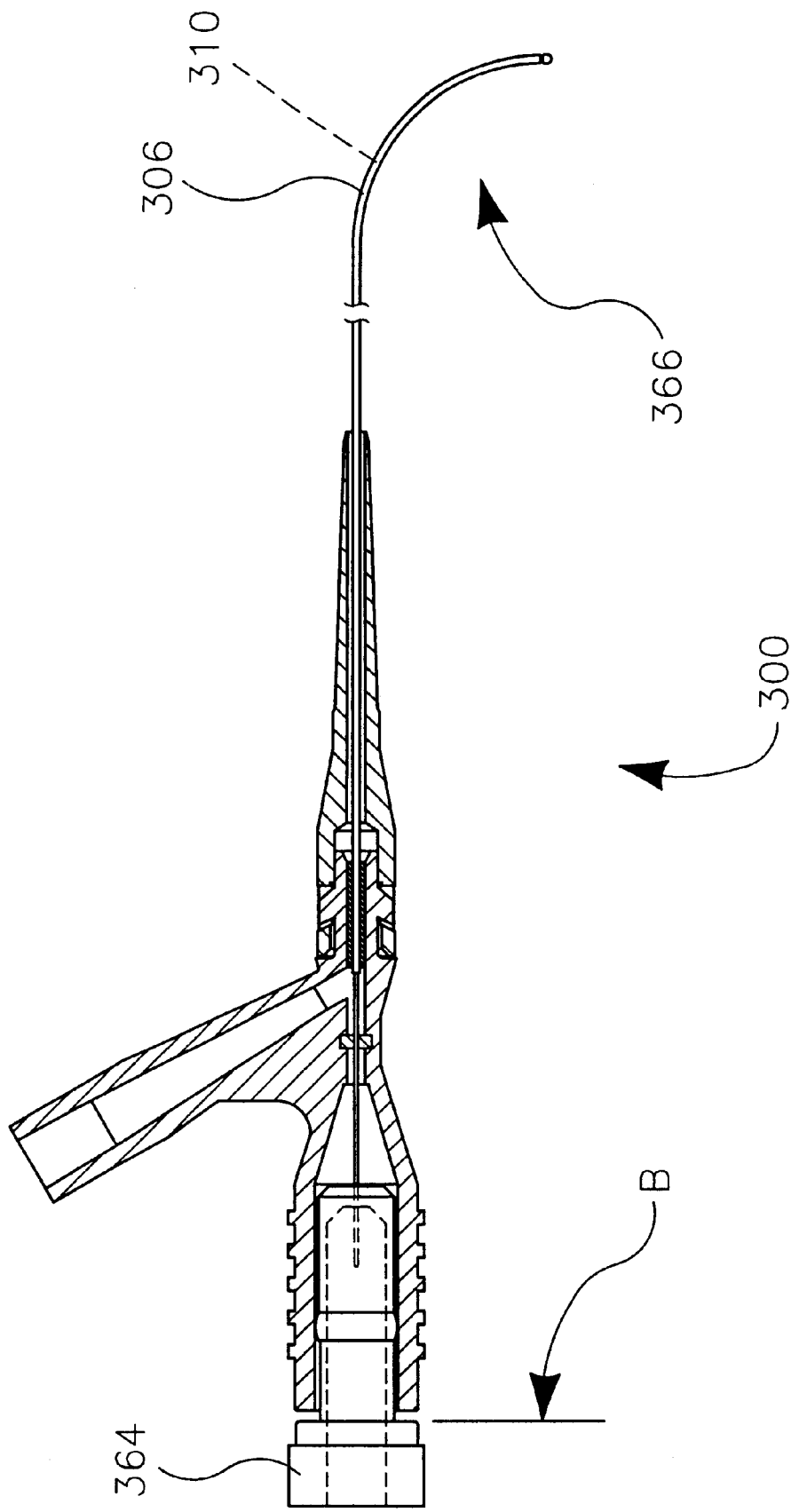
FIG. 9 is a plan view of a catheter in accordance with an exemplary embodiment of the present invention.

FIG. 9 is a plan view of catheter 300. In the embodiment of FIG. 9, slider 364 is disposed in a second position B. In FIG. 9 it may be appreciated that wire 310 includes a curved portion 366. When slider 364 is disposed in position A as illustrated previously, curved portion 366 of wire 310 is urged into a generally straight configuration. When slider 364 is disposed in position B as illustrated in FIG. 9, curved portion 366 of wire 310 is free to return to its unbiased, substantially curved shape.

Having thus described the figures, methods in accordance with the present invention may now be described with reference thereto. It should be understood that steps may be omitted from each process and/or the order of the steps may be changed without deviating from the spirit or scope of the invention. It is anticipated that in some applications, two or more steps may be performed more or less simultaneously to promote efficiency.

A method of fabricating a catheter in accordance with the present invention may begin with the step providing an elongate shaft defining a lumen. In the embodiment of FIG. 1, the elongate shaft is preferably comprised of hypodermic tubing. A length of hypodermic tubing may be formed utilizing extrusion and drawing processes.

The embodiment of FIG. 6 includes an elongate shaft comprising a wire defining a lumen proximate the distal end thereof A method in accordance with the present invention may include the step of removing material to form a lumen. Those of skill in the art will appreciate that many material removal processes may be utilized without deviating from the spirit and scope of the present invention. Examples of material removal processes which may be suitable in some applications include drilling with a rotating drill bit, laser drilling, and EDM drilling. Equipment suitable for EDM drilling is commercially available from Japax Incorporated of Yokohama, Japan.

A method in accordance with the present invention may include the step of cutting an elongate shaft to a desired length. Those of skill in the art will appreciate that a variety of cutting processes may be utilized without deviating from the spirit and scope of the present invention. Examples of processes which may be suitable in some applications include electronic discharge machining (EDM), electro-chemical machining (ECM), water jet cutting, LASER cutting, abrasive cutting, and mechanical cutting utilizing a cutting tool to remove material.

A method in accordance with the present invention may include the step of forming a bend in an elongate shaft to form a generally curved portion of the elongate shaft. The step of forming a bend may include the steps of placing a portion of the elongate shaft on a work surface, urging a radiused tool against the elongate shaft, and drawing the wire through the space between the radiused tool and work surface.

A method in accordance with the present invention may include the step of forming a coil. The step of forming a coil may include the steps of extruding a wire, drawing the wire to a desired diameter, and winding the wire around a mandrel. The step of forming a coil may also include the step(s) of cutting the wire to length before and/or after the winding process.

A method in accordance with the present invention may include the step of forming a tip member having a lumen. One method of forming a tip member having one or more lumens includes the steps of positioning a mandrel in a desired position and depositing molten metal around the mandrel. The molten metal may also be formed into a desired shape. The metal may be allowed to solidify, and the mandrel may be removed, leaving a lumen in the former location of the mandrel. An additional method of forming a tip member having a lumen includes the steps of forming a tip member, and removing material from the tip member to form a lumen. Those of skill in the art will appreciate that many material removal processes may be utilized without deviating from the spirit and scope of the present invention. Examples of material removal processes which may be suitable in some applications include LASER drilling, mechanical drilling with a rotating drill bit, and EDM drilling. Equipment for EDM drilling is commercially available from Japax Incorporated of Yokohama, Japan. In a presently preferred method a soldering process is utilized to form a tip member.

A method in accordance with the present invention may include the step of inserting an elongate shaft into a lumen defined by a coil and fixing the elongate shaft to the coil proximate their respective distal ends. Those of skill in the art will appreciate that many fixing processes may be utilized without deviating from the spirit and scope of the present invention. Examples of fixing processes which may be suitable in some applications include welding, soldering, brazing, adhesive bonding, and the use of a mechanical fastener. Examples of welding processes which may be suitable in some applications include LASER welding, TIG welding, resistance welding, and plasma welding.

A method in accordance with the present invention may include the step of removing material from an outer surface of an elongate shaft to produce a desired profile. Those of skill in the art will appreciate that many methods may be utilized to remove material from the outer surface of the elongate shaft. Examples of processes which may be suitable in some applications include grinding and turning on a lathe.

A method in accordance with the present invention may include the step of inserting a shaft assembly into the lumen of a sheath. In a presently preferred method, the sheath may be comprised of shrink tubing. A method in accordance with the present invention may include the step of heating the sheath and causing it to shrink. A number of methods may be used to apply heat to the sheath including convection, conduction and radiation. An example of heating with radiant energy is directing infrared energy from an infrared heat source at the material. Infrared energy sources suitable for this process are commercially available from Research Incorporated of Minnetonka, Minnesota. An example of heating with convection is directing a flow of hot air from a hot air gun so that it impinges on the material. Hot air guns suitable for this application are commercially available from Leister Elektro-Geratebau of Lucerne, Switzerland.

A method in accordance with the present invention may include the step of forming a hub proximate the proximal end of a shaft assembly. The proximal portion of the shaft assembly may be positioned inside a mold cavity and molten plastic injected into the mold. The molten plastic surrounds a portion of the shaft assembly. The molten plastic may be allowed to cool and solidify forming a hub. Methods in accordance with the present invention have also been envisioned in which the hub is mechanically or chemically adhered to the shaft assembly.

Figure 10:
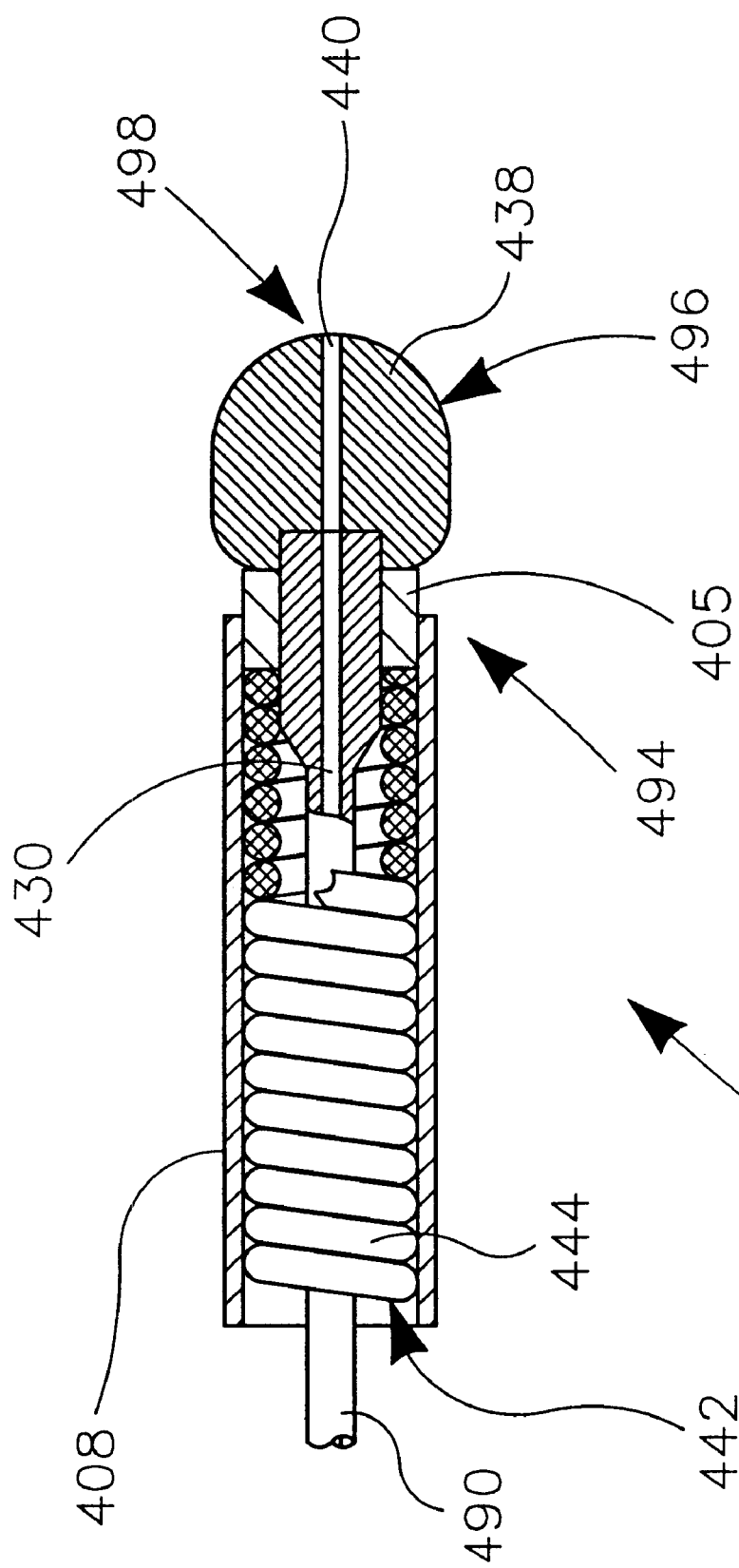
FIG. 10 is a cross-sectional view of a distal portion of a catheter in accordance with an additional exemplary embodiment of the present invention.

FIG. 10 is a cross-sectional view of a distal portion 403 of a catheter 400 in accordance with an additional exemplary embodiment of the present invention. In FIG. 10 it may be appreciated that catheter 400 includes electrode 496 comprising a tip member 438 which is fixed to a distal end 494 of an elongate shaft 490. Tip member 438 defines a tip lumen 440 which is in fluid communication with lumen 430 of elongate shaft 490 and distal port 498 of catheter 400. In a presently preferred embodiment, tip lumen 440 is disposed proximate the geometric center of electrode 496. During a PMR procedure fluid may be urged out of distal port 498 proximate a wound formed by electrode 496.

A marker band 405 is disposed about a portion of elongate shaft 490 proximate tip member 438 of electrode 496. In a preferred embodiment, marker band 405 comprises a radiopaque material. In this preferred embodiment, marker band 405 may comprise various radiopaque materials without deviating from the spirit and scope of the present invention. Examples of materials which may be suitable in some applications include gold, platinum, tungsten, iron, silver, and theroplastic material loaded with a radiopaque filler. Examples of radiopaque filler which may be suitable in some applications include barium sulfate, bismuth subcarbonate, bismuth trioxide, bismuth oxychloride, bismuth subcarbonate, tungsten, and depleted uranium.

In the embodiment of FIG. 10, a coil 442 comprising a plurality of turns 444 is disposed about a portion of elongate shaft 490 distal of marker band 405. Coil 442 is preferably fixed to elongate shaft 490 proximate a distal end thereof. A sheath 408 is disposed about coil 442 and elongate shaft 490. Embodiments of the present invention are also possible in which sheath 408 is disposed within a lumen defined by coil 442.

Figure 11:
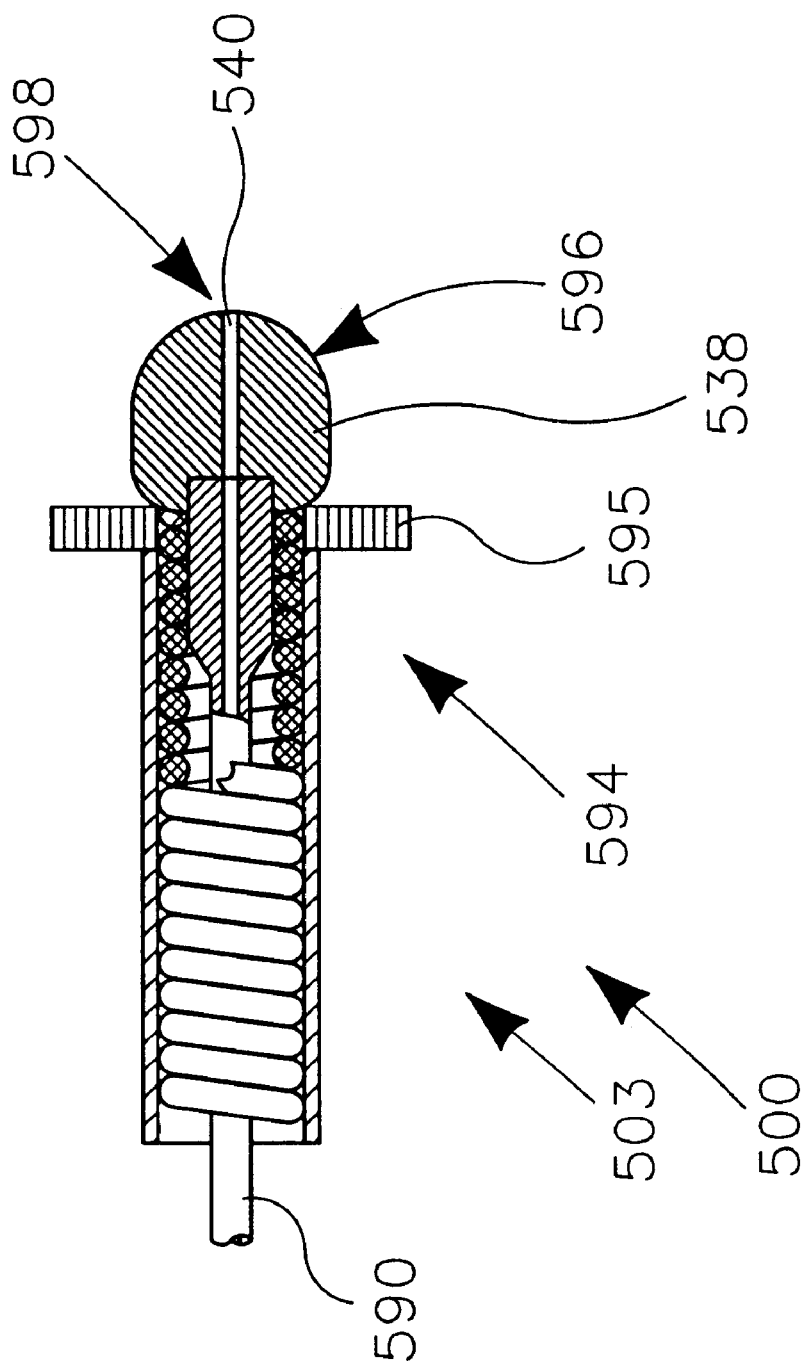
FIG. 11 is a cross-sectional view of a distal portion of a catheter in accordance with yet another exemplary embodiment of the present invention.

FIG. 11 is a cross-sectional view of a distal portion 503 of a catheter 500 in accordance with yet another exemplary embodiment of the present invention. In FIG. 11 it may be appreciated that catheter 500 includes electrode 596 comprising a tip member 538 which is fixed to a distal end 594 of an elongate shaft 590. A flange 595 is disposed about a portion of elongate shaft 590 proximate tip member 538 of electrode 596. In a preferred embodiment, flange 595 has a radial extent which is generally greater than the radial extent of tip member 538. In this preferred embodiment, flange 595 may assist in controlling the depth which electrode 596 penetrates into a target tissue during a PMR procedure. Fluid may be urged out of a tip lumen 540 and a distal port 598 defined by tip member 538 during a PMR procedure.

Figure 12:
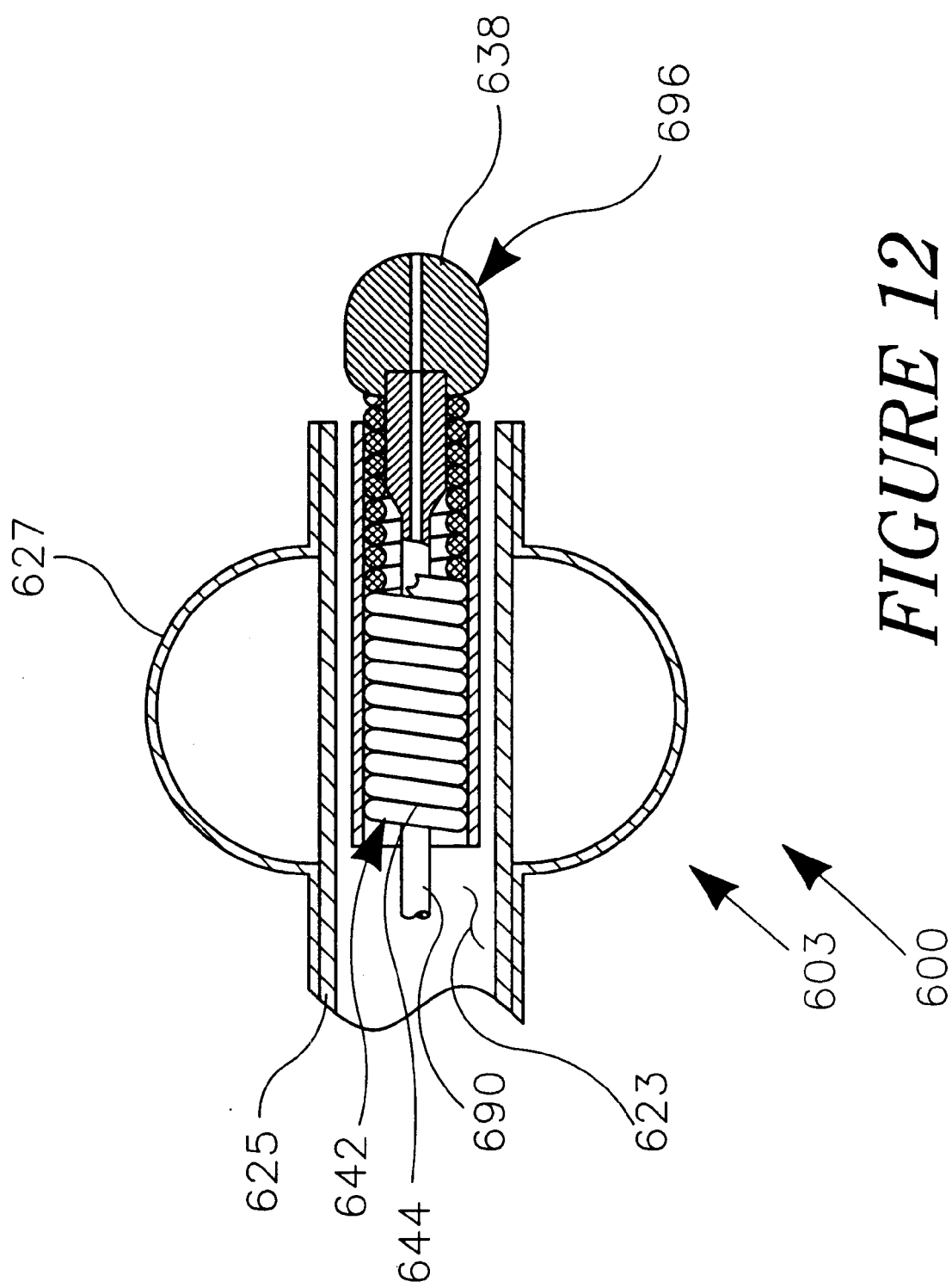
FIG. 12 is a cross-sectional view of a distal portion of a catheter in accordance with still another exemplary embodiment of the present invention.

FIG. 12 is a cross-sectional view of a distal portion 603 of a catheter 600 in accordance with still another exemplary embodiment of the present invention. In FIG. 12 it may be appreciated that catheter 600 includes an elongate shaft 690 and a coil 642 comprising a plurality of turns 644 disposed about a portion of elongate shaft 690. An electrode 696 comprising a tip member 638 is fixed to a distal end 694 of elongate shaft 690 and a distal end of coil 642. Catheter 600 is disposed within a lumen 623 defined by a guide member 625. A balloon 627 is disposed about guide member 625 proximate a distal end thereof. In a preferred embodiment, the longitudinal position of balloon 627 may be fixed relative to catheter 600. In this preferred embodiment, balloon 627 may assist in controlling the depth which electrode 696 penetrates into a target tissue during a PMR procedure. Balloon 627 preferably has a deflated state and an inflated state in which the radial extent of balloon 627 is generally enlarged. In the embodiment of FIG. 12, balloon 627 is shown in the inflated state.

Figure 13:
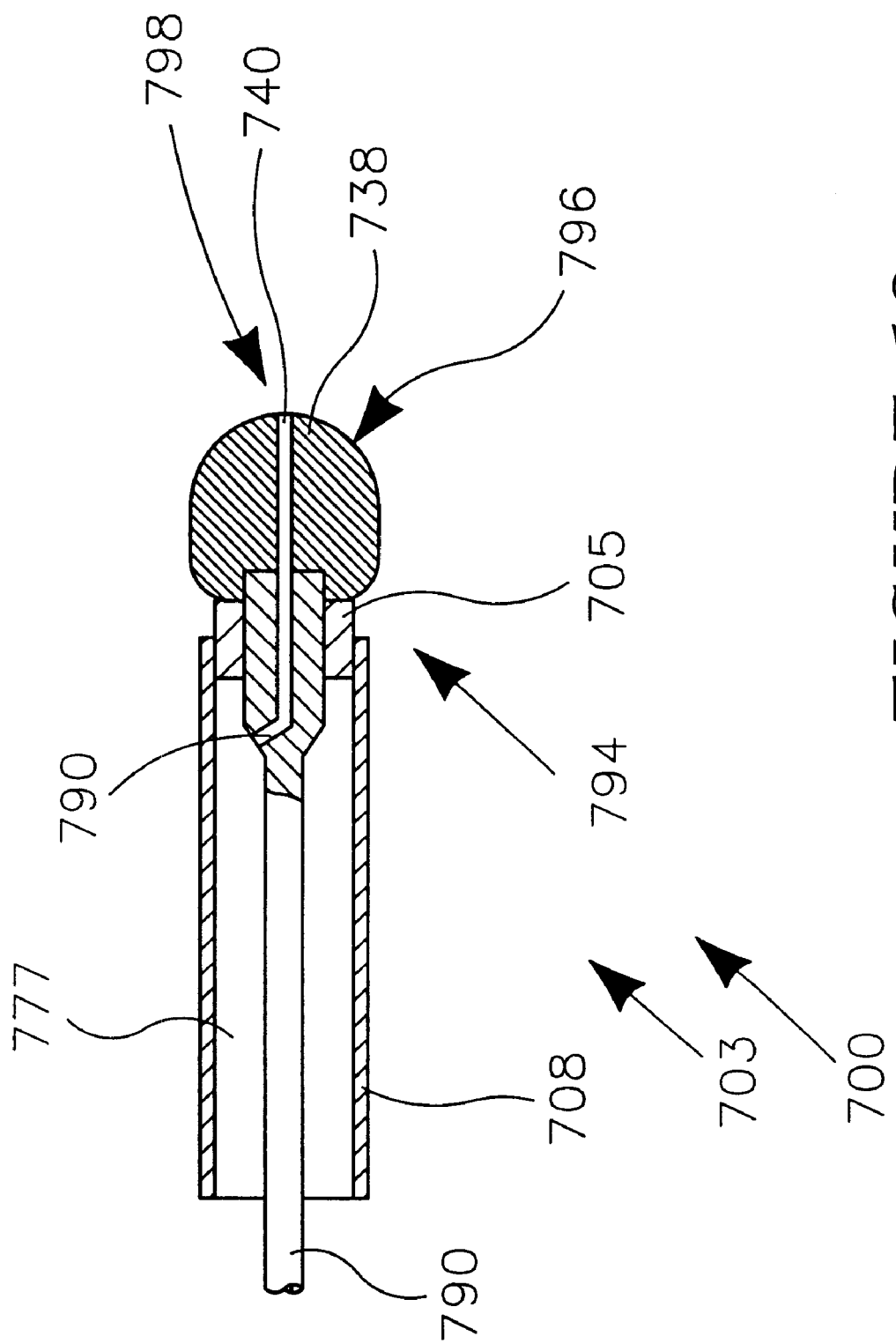
FIG. 13 is a cross-sectional view of a distal portion of a catheter in accordance with still another exemplary embodiment of the present invention.

FIG. 13 is a cross-sectional view of a distal portion 703 of a catheter 700 in accordance with yet another exemplary embodiment of the present invention. Catheter 700 of FIG. 13 includes an electrode 796 comprising a tip member 738 which is fixed to a distal end 794 of an elongate shaft 790. A marker band 705 is disposed about a portion of elongate shaft 790 proximate tip member 738 of electrode 796.

Marker band 705 is preferably fixed to elongate shaft 790, and a distal end of a sheath 708 is preferably fixed to marker band 705. In a preferred embodiment, marker band 705 comprises a radiopaque material. In this preferred embodiment, marker band 705 may comprise various radiopaque materials without deviating from the spirit and scope of the present invention. Examples of materials which may be suitable in some applications include gold, platinum, tungsten, iron, silver, and theroplastic material loaded with a radiopaque filler. Examples of radiopaque filler which may be suitable in some applications include barium sulfate, bismuth subcarbonate, bismuth trioxide, bismuth oxychloride, bismuth subcarbonate, tungsten, and depleted uranium.

Tip member 738 defines a distal port 798 of catheter 700. Distal port 738 is preferably in fluid communication with a shaft lumen 777 defined by sheath 777. In the embodiment of FIG. 13, distal port 738 communicates with shaft lumen 777 via a tip lumen 740 and a lumen 730 defined by elongate shaft 790. During a PMR procedure fluid may through shaft lumen 777, lumen 730, and tip lumen 740 so that it exits distal port 798 proximate a wound formed by electrode 796.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions scope is, of course, defined in the language in which the appended claims are expressed.

What is claimed is:

1. A PMR catheter, comprising:
    an elongate shaft having a proximal portion, a distal portion, and a lumen extending through at least the distal portion thereof, the distal portion having a predefined curve therein;
    an electrode disposed at or adjacent the distal portion of the elongate shaft;
    an electrode lumen defined by the electrode and being in fluid communication with the lumen of the elongate shaft; and
    a coil surrounding at least a portion of the elongate shaft, wherein the coil is selectively compressible around the elongate shaft to straighten the curve of the elongate shaft.

2. The catheter of claim 1, wherein the electrode comprises a tip member having a central axis and the electrode lumen is disposed in substantial co-axial alignment with the tip member.

3. The catheter of claim 1, wherein a distal end of the coil is fixed to the elongate shaft proximate the distal portion thereof by a weld joint.

4. The catheter of claim 1, further including a solder joint disposed between the elongate shaft and the coil.

5. The catheter of claim 1, wherein the elongate shaft comprises hypodermic tubing.

6. The catheter of claim 1, wherein the elongate shaft comprises hypodermic tubing including a nickel titanium alloy.

7. The catheter of claim 1, further including a sheath disposed about the coil.

8. The catheter of claim 1, further including a sheath disposed about the coil; wherein the sheath comprises polytetrafluoroethylene heat shrink tubing.

9. The catheter of claim 1, wherein the coil comprises a wire including a jacket disposed thereabout.

10. The catheter of claim 1, wherein the coil comprises a wire including a jacket disposed thereabout; and
    the jacket comprises polytetrafluoroethylene.

11. A PMR catheter, comprising:
    an elongate shaft having a proximal portion, a distal portion, and a lumen extending through at least the distal portion thereof;
    an electrode disposed at or adjacent the distal portion of the elongate shaft;
    an electrode lumen within the electrode that is in fluid communication with the lumen of the elongate shaft;
    a coil disposed about at least a portion of the elongate shaft,
    the coil including a proximal end, a distal end, and a plurality of turns, the distal end of the coil being fixed to the electrode;
    a hub disposed at the proximal portion of the elongate shaft,
    the hub defining a port lumen in fluid communication with the lumen of the elongate shaft and the electrode; and
    a mechanism at the proximal end of the catheter for selectively compressing the turns of the coil to change a curvature of the elongate shaft.

12. The catheter of claim 11, wherein the electrode comprises a tip member having a central axis and the electrode lumen is disposed in substantial co-axial alignment with the tip member.

13. The catheter of claim 11, wherein the distal end of the coil is fixed to the elongate shaft proximate the distal portion thereof by a weld joint.

14. The catheter of claim 11, further including a solder joint disposed between the elongate shaft and the coil.

15. The catheter of claim 11, wherein the elongate shaft comprises a wire including a nickel titanium alloy.

16. The catheter of claim 11, wherein the coil comprises a wire including a jacket disposed thereabout.

17. The catheter of claim 11, wherein the coil comprises a wire including a jacket disposed thereabout; and
    the jacket comprises polytetrafluoroethylene.

18. A PMR catheter, comprising:
    a shaft assembly including a lumen defined by a coil, an elongate shaft disposed within the coil lumen, and a sheath disposed about the coil;
    the elongate shaft having a proximal portion, a distal portion, and a lumen extending through at least the distal portion thereof;
    the lumen of the elongate shaft being in fluid communication with the lumen of shaft assembly;
    the elongate shaft including a curved portion;
    an electrode disposed at the distal portion of the elongate shaft;
    an electrode lumen within the electrode that is in fluid communication with the lumen of the elongate shaft;
    the coil having a distal end fixed to the electrode and the distal portion of the elongate shaft;
    a hub disposed at the proximal portion of the elongate shaft,
    the hub defining a port lumen in fluid communication with the lumen of the shaft assembly.

* * * * *